US00PP14529P29

(12) United States Plant Patent
Trees

(10) Patent No.: US PP14,529 P2
(45) Date of Patent: Feb. 10, 2004

(54) VERBENA PLANT NAMED 'BALAZPINK'

(50) Latin Name: *Verbena hybrida*
Varietal Denomination: Balazpink

(76) Inventor: Scott C. Trees, 725 Zenon Way, Arroyo Grande, CA (US) 93420

( * ) Notice: Subject to any disclaimer, the term of this patent is extended or adjusted under 35 U.S.C. 154(b) by 0 days.

(21) Appl. No.: 10/361,889

(22) Filed: Feb. 10, 2003

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Verbena plant named 'Balazpink', characterized by its outwardly spreading plant habit; medium green-colored leaves; and dark pink-colored flowers.

2 Drawing Sheets

Botanical classification/cultivar designation: *Verbena hybrida* cultivar Balazpink.

BACKGROUND OF THE INVENTION

The present Invention relates to a new and distinct cultivar of Verbena plant, botanically known as *Verbena hybrida,* and hereinafter referred to by the name 'Balazpink'.

The new Verbena is a product of a planned breeding program conducted by the Inventor in Arroyo Grande, Calif. The objective of the breeding program is to develop new freely flowering Verbena cultivars with an outwardly spreading growth habit. large full inflorescences and attractive leaf and flower coloration.

The new Verbena originated from a cross-pollination made by the Inventor in 2001 of a proprietary selection of *Verbena hybrida* identified as code number 236, not patented, as the female, or seed, parent with a proprietary selection of Verbena hybrida identified as code name verb-D, not patented, as the male, or pollen, parent. The cultivar Balazpink was discovered and selected by the Inventor as a flowering plant within the progeny from this cross-pollination in a controlled environment in Arroyo Grande, Calif.

Asexual reproduction of the new cultivar by cuttings taken at Arroyo Grande, Calif., since April, 2001, has shown that the unique features of this new Verbena are stable and reproduced true to type in successive generations of asexual reproduction.

SUMMARY OF THE INVENTION

The following traits have been repeatedly observed and are determined to be the unique characteristics of 'Balazpink'. These characteristics in combination distinguish 'Balazpink' as a new and distinct cultivar:

1. Outwardly spreading plant habit.
2. Medium green-colored leaves.
3. Dark pink-colored flowers.

Plants of the new Verbena differ primarily from plants of the parents in leaf shape and flower coloration.

The new Verbena can be compared to the cultivar, Sunmariripi, disclosed in U.S. Plant Pat. No. 11,037. However, in side-by-side comparisons conducted in West Chicago, Ill., plants of the new Verbena differed from plants of the cultivar Sunmariripi in the following characteristics:

1. Plants of the new Verbena had longer leaves than plants of the cultivar Sunmariripi.
2. Plants of the new Verbena had larger flowers and larger inflorescences than plants of the cultivar Sunmariripi.
3. Plants of the new Verbena had longer pedicels than plants of the cultivar Sunmariripi.
4. Flower color of plants of the new Verbena was lighter pink than flower color of plants of the cultivar Sunmariripi.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a flowering plant of 'Balazpink'.

The photograph on the second sheet is a close-up view of a typical inflorescence of 'Balazpink'. Flower and foliage colors in the photographs may differ slightly from the color values cited in the detailed botanical description which accurately describe the colors of the new Verbena.

DETAILED BOTANICAL DESCRIPTION

The cultivar Balazpink has not been observed under all possible environmental conditions. The phenotype may vary somewhat with variations in environment such as temperature and light intensity, without, however, any variance in genotype. The aforementioned photograph and following observations and measurements describe plants grown in West Chicago, Ill., under commercial practice in a polycarbonate-covered greenhouse with day temperatures ranging from 21 to 26° C., night temperatures ranging from 17 to 18° C. and light levels ranging from 5,000 to 8,000 foot-candles. Plants used for the photographs and description were about 12 weeks from planting rooted cuttings in 10-cm containers. In the following description, color references are made to The Royal Horticultural Society Colour Chart, 2001 Edition, except where general terms of ordinary dictionary significance are used.

Botanical classification: *Verbena hybrida* cultivar Balazpink.

Parentage:

*Female parent.*—Proprietary selection of *Verbena hybrida* identified as code number 236, not patented.

*Male parent.*—Proprietary selection of *Verbena hybrida* identified as code name verb-D, not patented.

Propagation:

*Type cutting.*—Stem cuttings.

*Time to initiate roots.*—About 7 days at 18° C.

*Time to develop roots.*—About 21 days at 18° C.

*Root description.*—Fibrous; whitish in color.

*Rooting habit.*—Freely branching.

Plant description:

*General appearance.*—Outwardly spreading plant habit; eventually trailing.

*Growth and branching habit.*—Freely basal branching; about six lateral branches develop per plant. Pinching, that is, removal of the terminal apices, enhances branching with lateral branches potentially forming at every node. Moderately vigorous.

*Plant height.*—About 10 cm.

*Plant diameter or spread.*—About 24.1 cm.

*Lateral branch description.*—Length: About 27.1 cm. Diameter: About 2 mm. Internode length: About 2.6 cm. Texture: Densely pubescent. Color: 144B.

*Foliage description.*—Arrangement: Opposite, simple. Length: About 4.5 cm. Width: About 2.4 cm. Shape: Ovate. Apex: Acute. Base: Truncate. Margin: Serrate. Texture, upper and lower surfaces: Pubescent. Venation pattern: Pinnate. Color: Young and fully expanded foliage, upper surface: 146A; venation, 145B. Young and fully expanded foliage, lower surface: 146B; venation, 145B. Petiole: Length: About 4.9 mm. Diameter: About 2 mm. Texture, upper and lower surfaces: Densely pubescent. Color, upper and lower surfaces: 145B.

Flower description:

*Flower type and habit.*—Single upright salverform flowers arranged on hemispherical corymbs. Freely flowering with about 26 flowers per inflorescence. Inflorescences positioned above and beyond the foliage. Flowers last about three to four days under greenhouse conditions. Flowers persistent. Flowers not fragrant.

*Flowering season.*—In the garden, flowering is continuous from spring until fall.

*Inflorescence height.*—About 4.4 cm.

*Inflorescence diameter.*—About 6.6 cm.

*Flower size.*—Diameter: About 2.7 cm. Tube length: About 2.3 cm. Throat diameter, distal: About 2.5 mm. Tube diameter, proximal: About 1.3 mm.

*Flower buds.*—Length: About 3.8 mm. Diameter: About 3.3 mm. Shape: Rounded. Color: Between 60C and 60D.

*Petals.*—Quantity/arrangement: Five per flower fused at base. Lobe length: About 1.1 cm. Lobe width: About 1 cm. Shape: Obovate. Apex: Emarginate. Margin: Entire. Texture, upper and lower petal surfaces: Glabrous, smooth. Texture, throat and tube: Pubescent. Color: When opening and fully opened, upper surface: Lighter than 68A; towards the throat, 155D. When opening and fully opened, lower surface: 68B; towards tube, 155D. Throat: 150C to 150D. Tube: 150D.

*Sepals.*—Quantity/arrangement: Five, fused into a tube. Length: About 1.2 cm. Diameter: About 2 mm. Shape: Linear. Apex: Acute. Margin: Entire. Texture, upper and lower surfaces: Densely pubescent. Color, upper and lower surfaces: 144C.

*Pedicels.*—Length: About 5.5 cm. Diameter: About 1.7 mm. Strength: Strong. Angle to stem: Acute. Texture: Densely pubescent. Color: 144B.

*Reproductive organs.*—Stamens: Quantity: Four per flower. Anther shape: Spade-like. Anther length: About 1 mm. Anther color: 150C. Pollen amount: Abundant. Pollen color: 150D. Pistils: Quantity: One per flower. Pistil length: About 2 cm. Stigma length: About 1 mm. Stigma shape: Funnel-like. Stigma color: Between N144C and N144D. Style length: About 1.8 cm. Style color: 150C. Ovary diameter: About 1 mm. Ovary color: N144C.

*Seed/fruit.*—Seed and fruit production has not been observed.

Disease/pest resistance: Plants of the new Verbena have not been observed to be resistant to pathogens and pests common to Verbena.

Temperature tolerance: Plants of the new Verbena have been observed to be tolerant to temperatures ranging from 2 to 40° C.

It is claimed:

1. A new and distinct cultivar of Verbena plant named 'Balazpink', as illustrated and described.

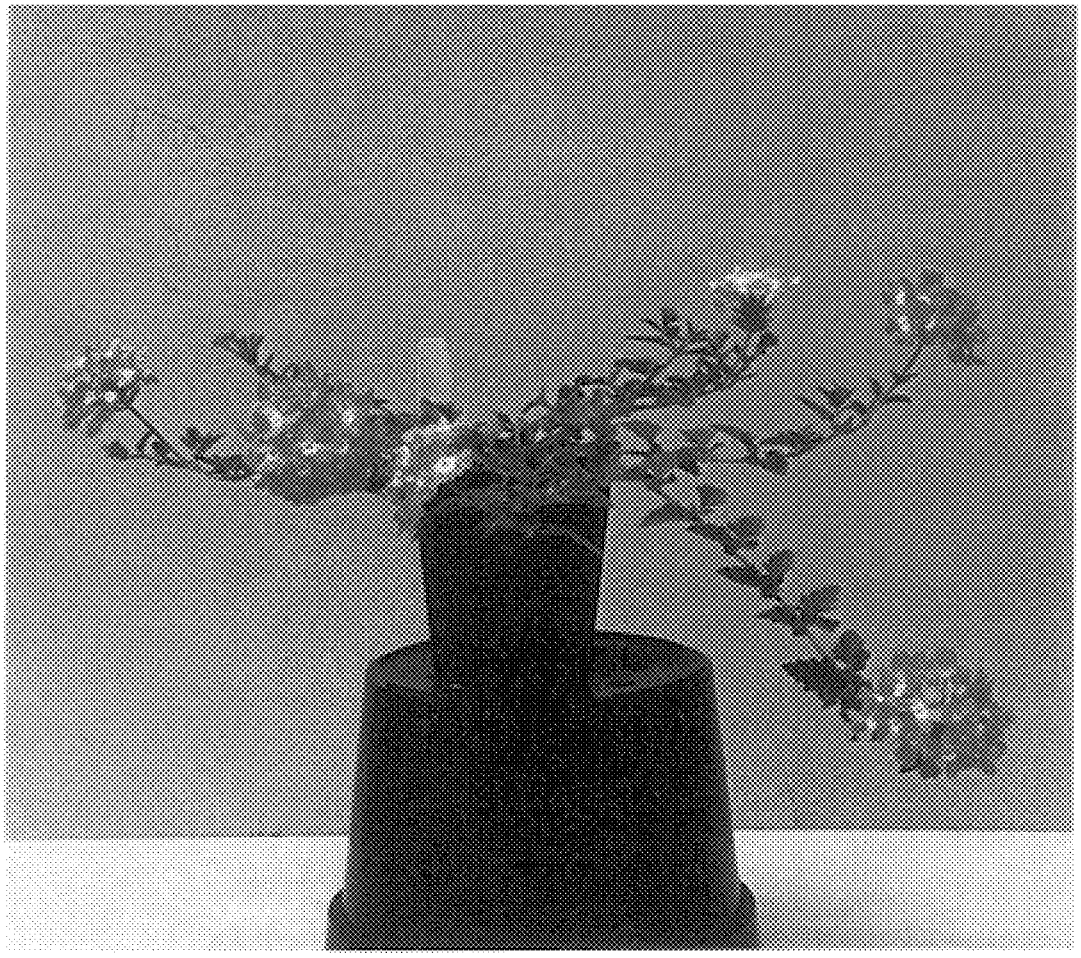

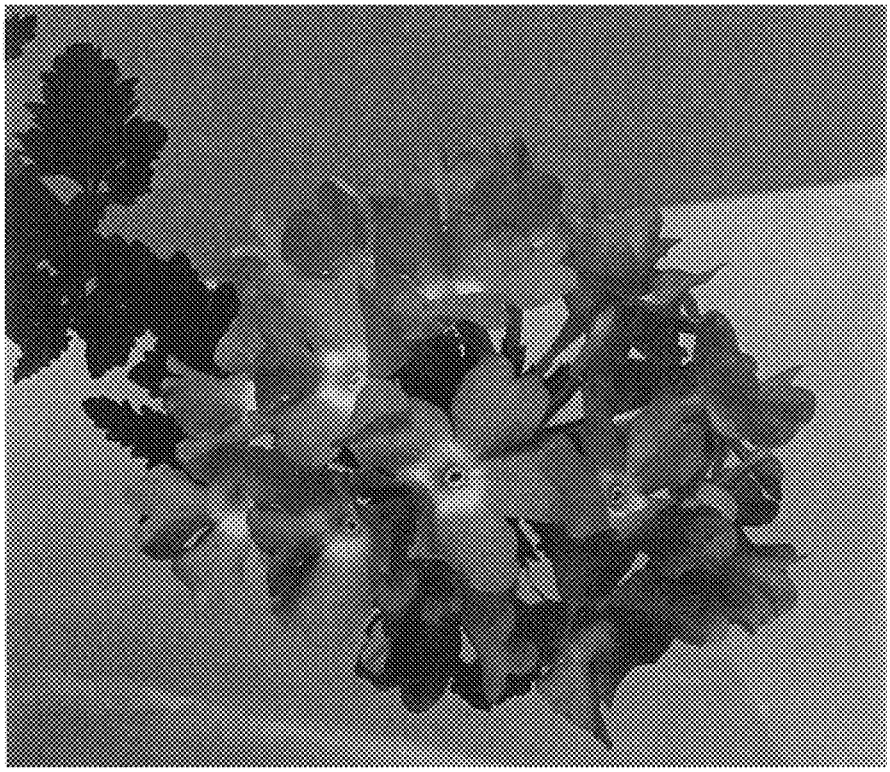

* * * * *